US007763470B2

(12) United States Patent
Babic et al.

(10) Patent No.: US 7,763,470 B2

(45) Date of Patent: Jul. 27, 2010

(54) TEST ELEMENT AND METHOD OF USE FOR ANALYZING BODY FLUIDS

(75) Inventors: Branislav Babic, Mannheim (DE); Martin Frank, Dirmstein (DE); Hans-Ludwig Griesheimer, Lampertheim (DE); Juergen Hoferer, Karlsruhe (DE); Rudolf Pachl, Ellerstadt (DE); Wilfried Schmid, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 317 days.

(21) Appl. No.: 11/859,757

(22) Filed: Sep. 22, 2007

(65) Prior Publication Data

US 2008/0060424 A1 Mar. 13, 2008

Related U.S. Application Data

(63) Continuation of application No. PCT/EP2006/002643, filed on Mar. 22, 2006.

(30) Foreign Application Priority Data

Mar. 22, 2005 (EP) .................................. 05102290

(51) Int. Cl.
*G01N 33/48* (2006.01)

(52) U.S. Cl. ............................. 436/63; 436/95; 422/58; 422/61

(58) Field of Classification Search ................... 436/63, 436/95; 422/58, 61
See application file for complete search history.

(56) References Cited

U.S. PATENT DOCUMENTS 4,774,192 A * 9/1988 Terminiello et al. ......... 436/530
5,104,640 A 4/1992 Stokes

FOREIGN PATENT DOCUMENTS

| | | |
|---|---|---|
| DE | 197 53 847 | 6/1999 |
| DE | 100 03 507 | 8/2001 |
| EP | 1 039 298 | 9/2000 |
| EP | 1 413 880 | 4/2004 |
| WO | WO 99/29435 | 6/1999 |
| WO | WO 2004/064636 | 8/2004 |

* cited by examiner

*Primary Examiner*—Lyle A Alexander
(74) *Attorney, Agent, or Firm*—Bose McKinney & Evans LLP

(57) ABSTRACT

An analytical test element for determining an analyte in a body fluid comprises a detection area in which the analyte is detected and an application site at which the body fluid can be applied to the test element. The application site is spaced apart from the detection area, wherein at least some of the body fluid applied to the application site moves from the application site to the detection area. The test element also comprises a contamination area which at least partially adjoins the application site, wherein an adhesive substance is applied to at least part of the contamination area of the test element. The adhesive substance adheres to the contamination area of the test element and is able to interact with an excess amount of applied body fluid such that at least some of the body fluid adheres to the test element and thereby an excess amount of body fluid remains in the contamination area. An additional embodiment provides for test elements which, after use, can be stored in a storage container. Another embodiment provides for the production of the test elements.

16 Claims, 4 Drawing Sheets

TEST ELEMENT AND METHOD OF USE FOR ANALYZING BODY FLUIDS

RELATED APPLICATIONS

This is a continuation application of International Application PCT/EP2006/002643, filed Mar. 22, 2006, which claims priority to EP 05102290.3, filed Mar. 22, 2005, which are hereby incorporated by reference in their entirety.

BACKGROUND

The analysis of body fluids allows an early and reliable detection of pathological conditions in clinical diagnostics and the specific and fact-based monitoring of physical conditions. More recently, the amount of blood required for individual analyses directed specifically towards one parameter is often only a few microliters to less than one microliter. For blood collection, skin, and in particular the finger pad or the earlobe of the person to be examined, is usually pierced with the aid of a sterile and sharp lancet. This method is particularly suitable when the blood sample can be analyzed immediately after it is collected.

Carrier-bound rapid tests have become established for chemical and biochemical analysis of body fluids in laboratories specialized for this purpose and are also used outside permanent laboratories. Such carrier-bound rapid tests based on specially developed dry chemistry can be carried out simply and with ease even by a layperson despite often complex reactions involving sensitive reagents. Common examples of carrier-bound rapid test devices are test strips used by diabetics for determining blood glucose concentration.

Analytical test elements for carrier-bound rapid tests typically comprise an application site on which the body fluid to be analyzed is applied and a detection area in which the particular analyte is detected. These strips are usually configured such that the sample is applied on top of and directly to the application area, in which case the application site lies above the detection area and the two areas may be separated by a fleece or the like. Alternatively, in the case of test strips having a capillary channel, the detection area is displaced relative to the application site, typically along the longitudinal axis of the test strip. This assembly has the advantage that the test element can be positioned in such a manner that the application site is situated in a readily accessible position outside of a measuring instrument, whereas the detection area is located inside the instrument. The evaluation unit is also located inside the instrument in a well-protected position next to the detection area. The test strip can remain in one position during the entire concentration determination and does not have to be moved into a measuring position after application of the sample. In the case of test strips that utilize capillary action to transport the sample, the sample is transported from the application site to the detection area by a transport element such as a capillary, absorbent fabric, or fleece that generates capillary action.

In the case of analytical test elements, and in particular those test strips providing a capillary action that are classified as "self-dosing," there is frequently an excess amount of blood at the site of application or on the outer sides or edges of the entrance to the capillary space after the measurement. The required handling to dispose of such a contaminated test strip is, on the one hand, not user-friendly and unhygienic, and, on the other hand, represents a contamination risk, especially in hospitals.

A similar hygiene problem arises when test elements are stored in a magazine and the magazine is inserted into a measuring instrument. Before the measurement, a test strip is moved by the instrument into an application position and after the measurement, the used test strip is returned back into the magazine and stored. This provides an advantage for the user such that she does not have to dispose of a test strip after each test. Once all test strips in the magazine are used, the magazine is removed from the measuring device and replaced by a new magazine. The used test elements are stored in the magazine and can therefore be hygienically handled and disposed of. A disadvantage of these systems is that, although the test strips are stored and sealed in the magazine before use to protect them from dirt and moisture, the individual storage chambers for the test strips are usually no longer closed and sealed after use. Thus, an excess amount of applied blood, which remains adhered to the used test strips, can crumble off over time and contaminate the instrument and, in particular, the evaluation optics or other instrument components through openings in the magazine.

U.S. Pat. No. 5,104,640 describes an adhesive agent used for blood on glass supports. In this case, polyvinyl pyrrolidone (PVP) is used as an additive in the alcohol fixation of blood smears. In the case of blood smears, blood is applied, smeared, and examined on a glass support (i.e., the site of application and the detection area are at the same site). The sample is spread as thinly as possible, because the blood substantially adheres to the glass support by adhesion forces without the use of an adhesive agent. PVP only supports this effect and, in this case, only has to adhere to a thin layer of blood.

SUMMARY OF THE INVENTION

The present invention addresses the disadvantages of the prior art and the above-mentioned problems. It provides a diagnostic test element which can be cost-effectively manufactured in large numbers and in which the application site is spaced from the detection area. Once body fluid has been applied to the test element, it adheres to the test element to prevent contamination of the environment. On the other hand, a gap between the application site and the detection area requires the sample to be transported. In order to ensure this sample is transported, the test element can be readily wetted and the body fluid can be transferred. Therefore, the present invention provides a test element which meets the goals noted above while also avoiding contaminating the measuring instrument.

An exemplary embodiment of the present invention provides analytical test elements which facilitate hygienic storage and disposal of used test elements. In particular, this embodiment concerns test elements which are stored after use in a storage container, wherein an adhesive substance is applied to the test elements and prevents superfluous body fluid from leaking or crumbling off. The test elements are coated in a fluid-conducting manner in the areas in which the body fluid can be applied, transported, and detected, and an adhesive substance can be applied in the areas which can be wetted with body fluid, but are not used for the measurement. This ensures that the body fluid can flow from the application site to the detection area and an analyte concentration can be determined there. At the same time, at least some of the superfluous body fluid can interact with the adhesive substance and adhere to the test element.

In one embodiment, an analytical test element used for determining an analyte in a body fluid comprises a detection area, in which the analyte is detected, and an application site to which the body fluid can be applied to the test element. The detection area is spaced apart from the application site and at least some of the body fluid applied to the application site passes from the application site to the detection area. The test element additionally comprises a contamination area which at least partially adjoins the application site, wherein an adhesive substance is applied to at least a portion of the contamination area. The adhesive substance adheres to the contamination area of the test element and is additionally able to interact with an excess amount of applied body fluid in such a manner that at least a portion of the body fluid adheres to and remains on the test element. In particular, portions of the body fluid that are not volatile are still retained on the test element.

In order to ensure that the body fluid automatically flows to the spaced apart detection area after being applied to the application site, a transport path is provided, for example, such that it can be easily wetted by the body fluid. A capillary active transport element is advantageously used for this and can be coated with a substance to make it hydrophilic. A diagnostic test element has several capillary active areas, including at the application site, in order to ensure that the body fluid can be applied to the test element, on the transport element, in order to transport the body fluid from the application site to the detection area, and in the detection area in which an analyte can be detected in the body fluid after the detection area has been wetted with the body fluid. Hydrophilizing methods can be used for this such as those mentioned in document WO 99/29435. The degree of wetness is usually sufficient if the liquid in the transport element has a concave meniscus, which occurs when the wetting angle is less than 90°.

A test element is understood as being any form of carrier-bound rapid tests for diagnostics, and especially rapid tests in strip form, such as test strips used for determining the blood glucose content in diabetics as described, for example, in documents WO 2004064636 and EP 1 039 298. The test elements are usually composed of several layers mounted on top of one another, which are generally laminated together or glued. These layers are usually made of plastic such as polyester. The base layer, for example, forms a so-called carrier layer on which a spacing layer can be glued and which forms a capillary. The capillary channel can be covered by a so-called cover layer.

An analyte is a component present in the body fluid (e.g., glucose, cholesterol, etc.) which reacts with a detection chemistry in the detection area such that, above a certain amount of analyte, the reaction can be measured in a measuring arrangement. In one embodiment, blood is used as the sample liquid in order to detect blood glucose as an analyte in the detection area and to determine the concentration of blood sugar.

In addition to blood, interstitial fluid and other endogenous fluids can also be used as body fluids. It is also possible to not only detect one analyte (e.g., blood glucose), but also to detect several analytes, e.g., glucose and glycosylated hemoglobin (HbA1c), and to detect them in one body fluid (e.g., blood) as well as in a mixture of several body fluids (e.g., blood and interstitial fluid).

The analyte can react with a detection chemistry and generate a measuring signal in the detection area. The measuring signals can, for example, be detected by a detection unit in order to thus determine the concentration of the analyte in the body fluid. In the case of photometric test strips, the signal can be a change in color. In the case of electrochemical systems, a current or other electrical signal is generated. Furthermore, it is also possible that there is no detection chemistry in the detection area and the sought-after analyte is determined by optical reflectance and/or transmission measurement.

The application site refers to the location at which body fluid is applied by the user to the test element. From there the body fluid is transferred to the detection area, for example, by capillary forces. The application site is spaced apart from the detection area. The analytical test element can comprise a transport element which transports body fluid from the application site to the detection area.

The adhesive substance is advantageously applied in an area that can be contaminated with body fluid, referred to as the so-called "contamination area." The contamination area is an area which can be reached by the excess amount of body fluid, such as blood, and especially during application of blood on the test element. The contamination area at least partially adjoins the application site. The contamination area can consist of several non-contiguous subareas, for example, including several portions or sides next to the application site such as on the bottom surface of the carrier layer or on the top surface of the cover layer. If a transport element is present, the adhesive substance can also be located next to or along the transport element. An adhesive substance is not absolutely necessary on the cut edges because the risk of dried blood crumbling off is especially high when a large amount of excess blood is present. Such a large drop of blood or body fluid extends due to its spatial dimensions to the carrier or cover layer which thus ensures that the drop comes into contact with the adhesive substance. If the transport element is a capillary, the adhesive substance can, for example, be applied around the capillary.

Various embodiments are conceivable for the structure of the transport element. For example, the transport element can have a capillary and advantageously comprises a capillary channel or a capillary gap, but it is also possible to use a type of wick or fleece. The transport element can be an independent component, e.g., an additional capillary, or it can be integrated into the analytical test element in the form of a groove or capillary channel, which is formed when a spacer layer containing a capillary slot is applied to a carrier layer and a cover layer is applied thereon. In addition, the transport element can be coated with a hydrophilic layer. Thus it can, for example, be hydrophilized in order to improve the transport of body fluid. In addition or in the alternative, negative pressure can be used to assist the transport of fluid into the detection area.

The detection area can also be covered with a type of fleece which serves as a transport element, protects against contamination, and can also be used to separate certain components of the body fluid (e.g., erythrocytes from the blood) and/or to uniformly disperse the body fluid in the detection area by a so-called spreading of the liquid. The fleece can be positioned between the detection area and the application site located on the top surface of the fleece, for example, in embodiments of top loaded test strips. Consequently, in such a test element, sample transport takes place perpendicularly to the longitudinal axis of the test strip. However, the fleece can also be laterally displaced relative to the detection area or to the application site, especially in the case of capillary test strips. In this embodiment, the fleece can lie on the detection area under the application site or between the two areas.

An adhesive substance is understood as being a substance that causes an excess amount of body fluid, in particular blood and interstitial fluid, to remain on the analytical test element after the body fluid has dried and, in particular, does not crumble and fall off under mechanical strain when the analytical test strip is handled, or after use and during storage (in particular, when used test elements are retracted into a magazine or during disposal). The aqueous components of the body fluid advantageously solubilize the adhesive substance, resulting in the adhesive substance mixing with the body fluid. Evaporation of the mixture occurs, for example, in a period of approximately 10 to 20 minutes and the dried substance containing the bound body fluid adheres to the analytical test element. The drying period, of course, depends on the environment, in particular, ambient temperature and humidity, and thus can vary greatly. Adhesive substances are also conceivable which ensure that the sample adheres to the test element immediately after contact with the sample fluid.

The actual measuring process to determine the analyte in the body fluid is independent of this process and thus the drying period also has no effect on the time required for a measurement cycle. The method is such that after a measurement, the analytical test element is transported back into a magazine and is stored there. The measurement cycle is usually considerably shorter than the above-mentioned drying period because excess blood that may be present may not have dried by the time the test strip is pushed back into the magazine. The excess blood on the test strip dries while the used test strip is stored in the magazine and thus prevents dried blood from crumbling off and contaminating parts of the instrument, the optical system, or the environment.

In one embodiment, the adhesive substance is not applied to the application site and/or to the transport element since this can cause less sample liquid to be available for measurement, because some of the sample can interact with the adhesive substance and not reach the detection area. Furthermore, the adhesive substance may enter the detection area together with the sample and have an unfavorable effect on the measurement. If the adhesive substance is in the detection area, it can impair the application of the detection chemistry, the fixation and/or storage life of the dried chemistry, or the measurement itself.

If the adhesive substance is nevertheless applied to the application site, the transport element, and/or the detection area in order to simplify the manufacturing process, the adhesive substance is selected such that it does not have an adverse effect on the measuring process. The analytical system is then adapted accordingly, e.g., such that an increased required sample volume can be accepted.

The adhesive substance is a substance that advantageously does not have a self-absorbing volume, but can prevent detachment of an excess amount of dried body fluid and, in particular blood, by making an adhesive bond between the body fluid and the test element. For example, the aqueous portions of the blood solubilize the adhesive substance, which results in a firm contact between the body fluid and the carrier material after the body fluid has dried. The adhesive substance does not produce a capillary effect which would compete with the capillary at the application site for the sample liquid. The adhesive substance generates, in particular, a delayed action compared to the capillary at the application site so that the detection area is filled first with a body fluid sample and only liquid that has been applied in excess is held by the adhesive substance. The attractive force with which the adhesive substance acts on the sample is advantageously less than the capillary force with which the sample is transported into the detection area, at least immediately after sample application, to thus ensure that the detection area is filled first and only the body fluid that has been applied in excess adheres together with the adhesive substance to the test element.

If an absorbent substance were to be used such as a sponge or a rough surface instead of using a non-absorbent adhesive substance, this substance would compete with the test strip capillary due to its own capillary action and the required spatial proximity to the test strip capillary or the application site, resulting in an increase in the required sample volume. One reason for this is because at least some of the sample would be absorbed by the absorbent substance during the filling process of the detection area.

The adhesive substance is advantageously applied during production of the test strip and as a result is mechanically bound with the test element such that the adhesive layer is not removed by mechanical strain such as bending, torsion, or abrasion in the subsequent process steps nor during handling and transport. The excess amount of body fluid which binds to the adhesive substance should adhere strongly to the test element after it has dried such that it remains on the test element during handling by the user, disposal of the test strip, and in particular, during storage. The binding of the adhesive substance to the test element and the binding of the dried excess amount of body fluid in interaction with the adhesive substance on the test element can, for example, be of a physical and/or chemical type (e.g., it can be covalent bonding, hydrogen bonding, and the like). For example, the adhesive substance swells up when it comes into contact with the liquid and, while the body fluid evaporates, it forms a sticky paste which adheres to the test element.

The adhesive substance contains components of water-soluble adhesives. Suitable adhesive substances, for example, contain dextrin or caoutchouc. Polyvinyl acetate (PVAc) has proven to be a particularly suitable component of the adhesive substance. For example, an aqueous dispersion containing 35% by weight PVAc is applied to the analytical test element in a coating thickness of approximately 60 μm. The dispersion is subsequently dried for about 30 seconds at approximately 70° C. and then results in an approximately 17 μm thick dry layer on the test element. PVAc can, for example, be obtained under the trademark Vinnapas® from Wacker Chemie AG, Munich, Germany (typical molar weights are 1000-100,000 g/mol). The adhesive substance can, for example, be applied with a coating knife, by spraying, dipping, printing (e.g., screen printing or pad printing), or pouring. Dextrin can also be used as an adhesive substance, but it should be noted that the functional efficiency of dextrin diminishes considerably under very dry conditions. This is of importance when the test strips are stored after use in the same chambers of the storage container in which they were stored before use. The magazines usually contain desiccants to provide a dry environment for the detection area before use, because the detection chemistry in the detection area is moisture-sensitive. When selecting the adhesive substance this should be advantageously taken into consideration.

Care should be taken that the adhesive substance adheres well to the plastic layers that are used. This is, for example, the case for PVAc, dextrin, or caoutchouc, which bind well to the advantageously used polyester layers. When using dextrin as an adhesive substance, a 10% dispersion is applied in a layer thickness of about 120 μm and dried.

The production of an analytical test element for determining an analyte in a body fluid comprises a detection area for detecting an analyte in a body fluid, an application site at which a body fluid can be applied to the test element, wherein the detection area is spaced apart from the application site and wherein at least a portion of the body fluid applied to the application site reaches the detection area from the application site, and a contamination area which at least partially adjoins the application site. A process for producing an analytical test element with an adhesive substance, for example, comprises the following steps:

(1) Applying an adhesive substance to the contamination area where the contamination area is at least partially composed of plastic and is arranged on a carrier and/or cover layer such that the adhesive substance at least partially adheres to the plastic of the contamination area. Accordingly, the adhesive substance is able to interact with the excess amount of body fluid applied to the test element in such a manner that at least a portion of the body fluid adheres to the test element and the excess amount of body fluid remains in the contamination area;

(2) drying the adhesive substance on the carrier and/or cover layer; and (3) assembling the carrier and cover layer to form an analytical test element.

The adhesive substance can be applied, for example, over the entire area of the layer or only on parts thereof. If the test strip consists of a carrier layer and a cover layer such that a capillary is formed between them with or without a spacer layer, it is advantageous to coat the bottom surface of the carrier layer and the top surface of the cover layer with the adhesive substance. In such an embodiment, the carrier and cover layer are mounted in such a manner that the top surface of the carrier layer faces the bottom surface of the cover layer and thus the capillary that is formed between the two layers is not coated with the adhesive substance. The top surface of the carrier layer and/or the bottom surface of the cover layer can be at least partially coated with a hydrophilic substance. The carrier or the cover layer can have an opening in the area of the application site through which the hydrophilic coating is accessible and exposed so that the body fluid can be easily applied to the hydrophilic layer. The opening can, for example, be produced by punching one of the two layers before gluing the two layers together. An advantage of this is that the adhesive substance on the top surface of the cover layer and on the bottom surface of the carrier layer can be applied over a large area without having to screen the application site. Subsequent punching of the cover layer exposes the hydrophilic layer of the application site.

After applying the adhesive substance, it is dried for 30 seconds at 70° C. Subsequently, the layers can be processed as usual to form an analytical test element. The process of applying the adhesive substance to the analytical test element does not interrupt the usual production process for manufacturing the analytical test element, but rather it is a prior process step in which the layers, and in particular the carrier and the cover layer, are subjected to pretreatment. After the drying step, the adhesive substance is mechanically stable and the coated layers can run through the usual production process.

In the case of an analytical test element which does not have a cover layer and advantageously has one layer, the process for producing the test strip can comprise the following steps:

(1) applying the adhesive substance to the contamination area of the carrier layer, which at least consists partially of plastic in the contamination area, wherein the adhesive substance adheres at least partially to the plastic of the layer and is able to interact with an excess amount of body fluid applied to the test element in such a manner that at least some of the body fluid adheres to the test element and the excess amount of body fluid remains on the contamination area;

(2) drying the adhesive substance on the carrier layer; and (3) applying the reagent to the detection area of the carrier layer, whereby this step can take place before or after applying the adhesive substance.

The adhesive substance is advantageously applied to the top surface of the carrier layer either completely on the entire area or on only parts of the carrier layer. The detection area can, for example, be applied to the adhesive substance or to areas of the carrier layer on which there is no adhesive substance. For example, the reagent is applied to the adhesive substance on the carrier layer where at least a portion of the detection area is not covered with the adhesive substance.

Another embodiment for producing an analytical test element can comprise the following steps:

(1) applying the detection area to a carrier layer, advantageously to the top surface of the carrier and usually only to a small area of the carrier layer;

(2) applying the adhesive substance to the carrier layer, whereby at least a portion of the detection area is not covered with the adhesive substance; and (3) subsequently drying the adhesive substance on the carrier layer of the analytical test element.

A structured coating can, for example, be achieved by a screen printing process using a mask which screens at least a portion of the detection area, or by pad printing using a printing stamp which has a corresponding recess.

In another embodiment of the invention, one or more analytical test elements are provided to the user in a storage container (magazine), wherein adhesive substance is applied to the test elements so that an excess amount of body fluid remains in the contamination area. For example, one or more test elements to which an adhesive substance has been applied are stored in a storage container and the analytical test elements are stored (re-stored) after use in the same or in a different magazine.

In most magazines containing analytical test elements, the test strips are sealed before use and tightly packaged to protect them against environmental influences. In order to use the test strips, the seal is broken and the test strips, if they are returned to the magazine, are present in open chambers after use. In order to prevent contamination by dried body fluid that has been applied in excess, the used test strips after being returned to the magazine must also be tightly packaged again in the same or in a different magazine which is technically very complicated. The application of an adhesive substance to the analytical test elements offers a simple solution, because the adhesive substance adheres to the contamination area of the test element and is able to interact with body fluid that has been applied in excess to the test element in such a manner that at least some of the body fluid adheres to the test element and the excess amount remains in the contamination area. The analytical test elements can therefore be especially used for systems in which the test strips are returned to a magazine after use. Advantageously, adhesive substances are also used to which the sample adheres immediately after sample application. In this embodiment, it is possible to prevent contaminating the device during transport of a used test strip back into the magazine.

In another embodiment, a system for determining the concentration of an analyte in a body fluid comprises one or more analytical test elements and a storage container (magazine) for these test elements, wherein the test elements are stored in the storage container after use. Furthermore, the system comprises a measuring instrument with an evaluation unit in which the detection area can be evaluated in order to thus determine the concentration of the analyte.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

Corresponding reference numerals are used to indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
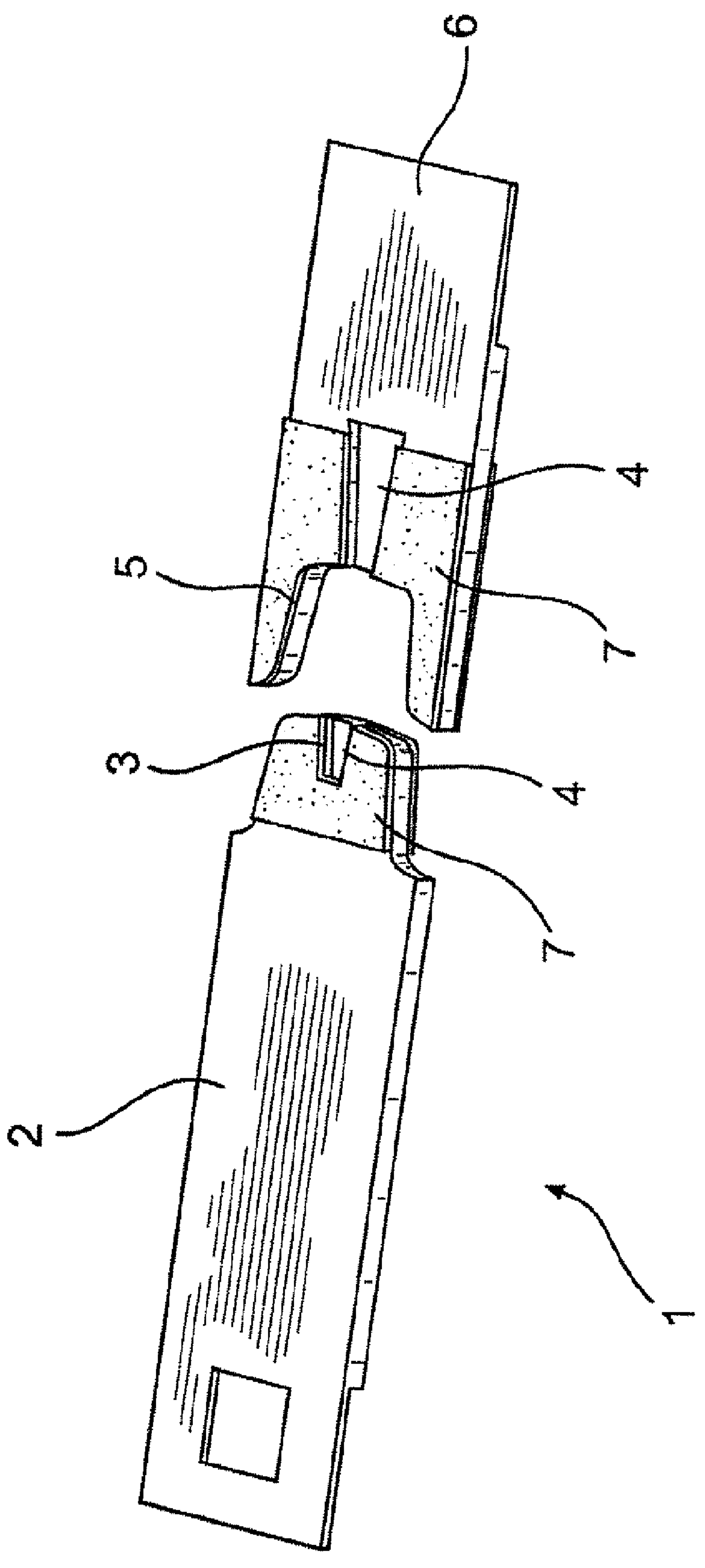
FIG. 1 is a perspective view of an analytical test unit.

FIG. 1 shows an example of an analytical test element 1 which comprises a cover layer 2 and a carrier layer (not shown). The cover layer 2 has a recess 3 at the application site to which body fluid is applied and a hydrophilic intermediate layer 4 is accessible in the recess 3. During production, a strip 7 being approximately 7 mm wide, for example, and coated with an adhesive substance in a previous process step, is laminated onto a tape having a plurality of contiguous test elements on the top surface of the cover layer 2. Additionally, an optional second strip is laminated onto the bottom surface of the carrier layer in the contamination area at the tip of the test element. The test element tape is subsequently divided into individual test elements. The edge trimming is punched out along a contour 5 before or after the dividing and a single test strip remains having, for example, a 2.8 mm wide blood adhesion middle strip in the area of the blood application notch 3. The residual section 6 is discarded.

Figure 2:
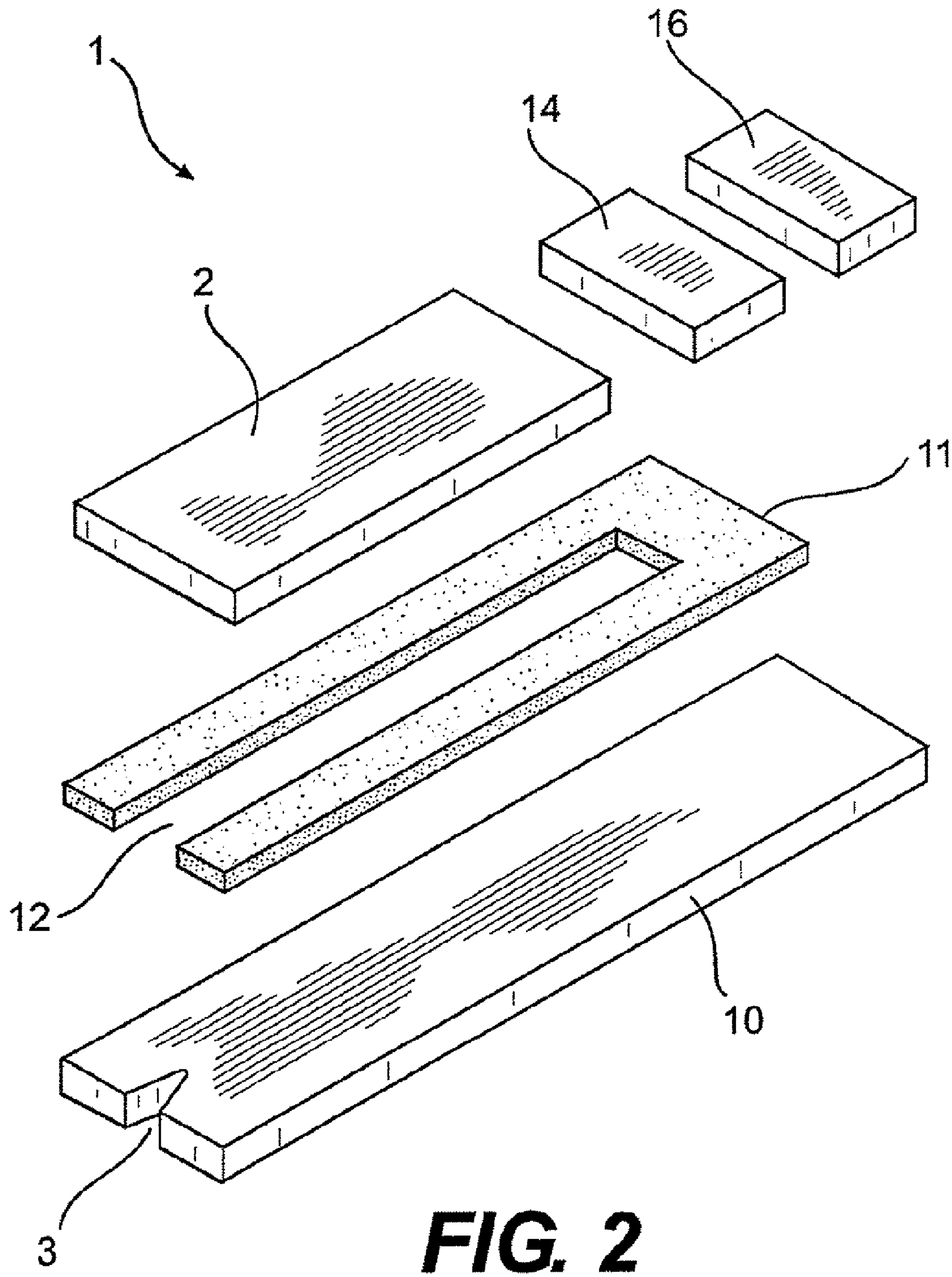
FIG. 2 is an exploded perspective view of an analytical test unit having a spacer layer with a capillary channel.

FIG. 2 shows an analytical test element 1 with a recess 3. A spacer layer 11, which determines the contour and the height (corresponding to the thickness of the spacer layer 11) of a capillary-active channel 12, is located on a carrier layer 10 into which the recess 3 is introduced in the form of a V-shaped notch and can be used to mark the application site. The spacer layer 11 consists of a double-sided adhesive tape to which, for example, active charcoal has been added to the adhesive paste. A cover layer 2, a detection area 14, and a protective layer 16 lie on top of this spacer layer 11. The recess 3 and detection area 14 are mounted closely next to one another such that the capillary-active zone 12 extends from the free edge of the recess 3, being located above the recess or notch 3, to the opposite free edge of the detection area 14. The recess in the spacer layer 11 which determines the shape of the capillary-active channel 12 is slightly longer than the cover layer 2 and detection area 14 together so that an uncovered gap of usually a few millimeters in width remains from which air can escape when the capillary-active zone 12 is filled with sample liquid. This gap also remains uncovered by the protective layer 16 to ensure that its function remains. The protective layer 16 should prevent exposed areas of the adhesive tape from causing an undesired adhering of the test element to surrounding objects. The contamination area is located in the area surrounding the recess 3, especially on the top surface of the cover layer 2 and on the bottom surface of the carrier layer 10. In one embodiment, an adhesive substance is applied at least in a portion of this area. Advantageously, an adhesive substance is applied to the entire top surface of the cover layer 2 and to the entire bottom surface of the carrier layer 10, wherein the recess 3 ensures that the capillary channel 12 is accessible and free of the adhesive substance.

FIGS. 3 to 6 describe an exemplary embodiment of a magazine or storage container 20 in which analytical test elements 1 are stored (returned to a magazine) after use. The storage container 20 is inserted into a measuring instrument (not shown). In order to carry out a measurement, the test element 1, which comprises a detection area 14, is pushed by the instrument out of the storage container 20 into an application position, and after application of body fluid, it is optionally moved into a second measuring position in order to be analyzed there. After the measurement, the used test element 1 is pulled back into the storage container 20. In this embodiment, an adhesive substance is applied to the test element 1 in the contamination area such that an excess amount of applied body fluid remains on the analytical test element 1 and does not contaminate the inside of the device. Without the use of the adhesive substance, it would be possible, for example, for dried blood to detach from the test element 1 and enter the inside of the instrument through an engaging hole 23 or an ejection opening 25.

The storage container 20 is formed by a drum magazine 21 designed as a cylindrical injection-molded plastic part. Guide chambers 22 are circumferentially arranged therein and extend continuously in the axial direction between an engaging hole at the front end 23 for a drive unit 24 and an opposing ejection opening 25. The drum magazine 21 has a central bore 26 with gear teeth on the edge 27 for a step switching system (not shown) to align the test element to be pushed out in the propulsion axis of the drive unit 24. Axial blind holes 28 for receiving a desiccant 29 are arranged radially displaced towards the outside. To protect against damaging the environment, the front faces of the guide chambers 22 are closed by a sealing foil (not shown).

Figure 3:
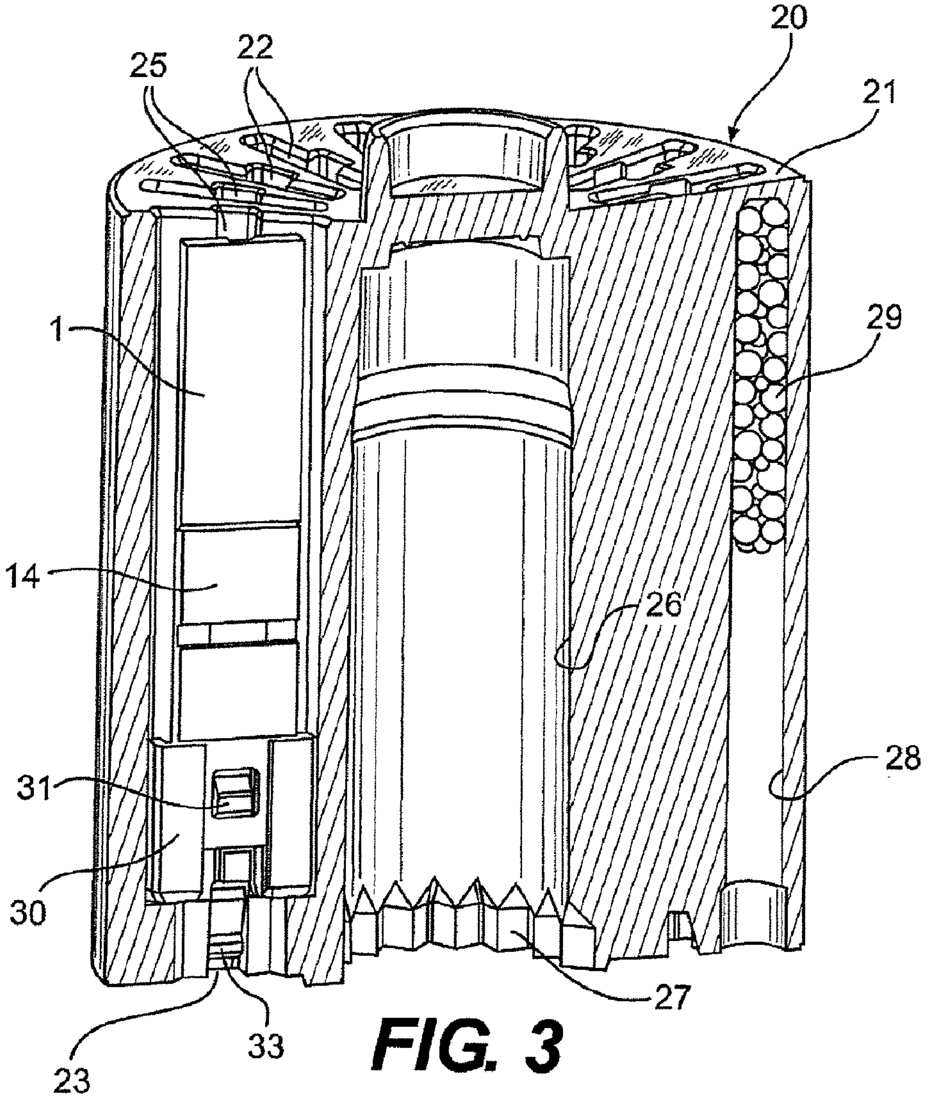
FIG. 3 is a perspective view in partial cross-section of a storage container for holding test elements.
Figure 4:
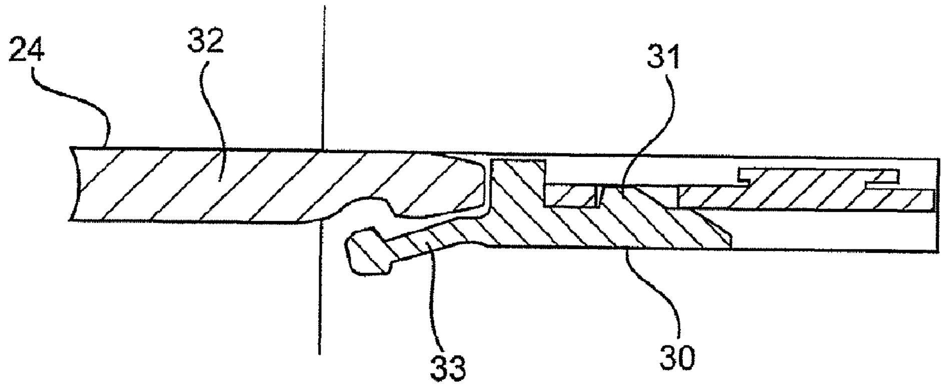
FIG. 4 is a cross-sectional view of a carriage of the container of FIG. 3 and a plunger which drives the carriage.

In the embodiment shown in FIGS. 3 and 4, the test elements 1 are held in a carriage 30 for better guidance and which moves longitudinally like a drawer in the respective guide chamber 22. The carriage 30 embraces an end section of the test element 1 and is connected to the element by a latching nose 31. A single holding claw 33 of the carriage 30 is provided as a driving carrier for a positive connection to a single plunger 32. This arrangement enables the test element 1 to be pushed out in order to carry out a measurement and for the used test element 1 to be retracted back into the magazine.

Figure 5:
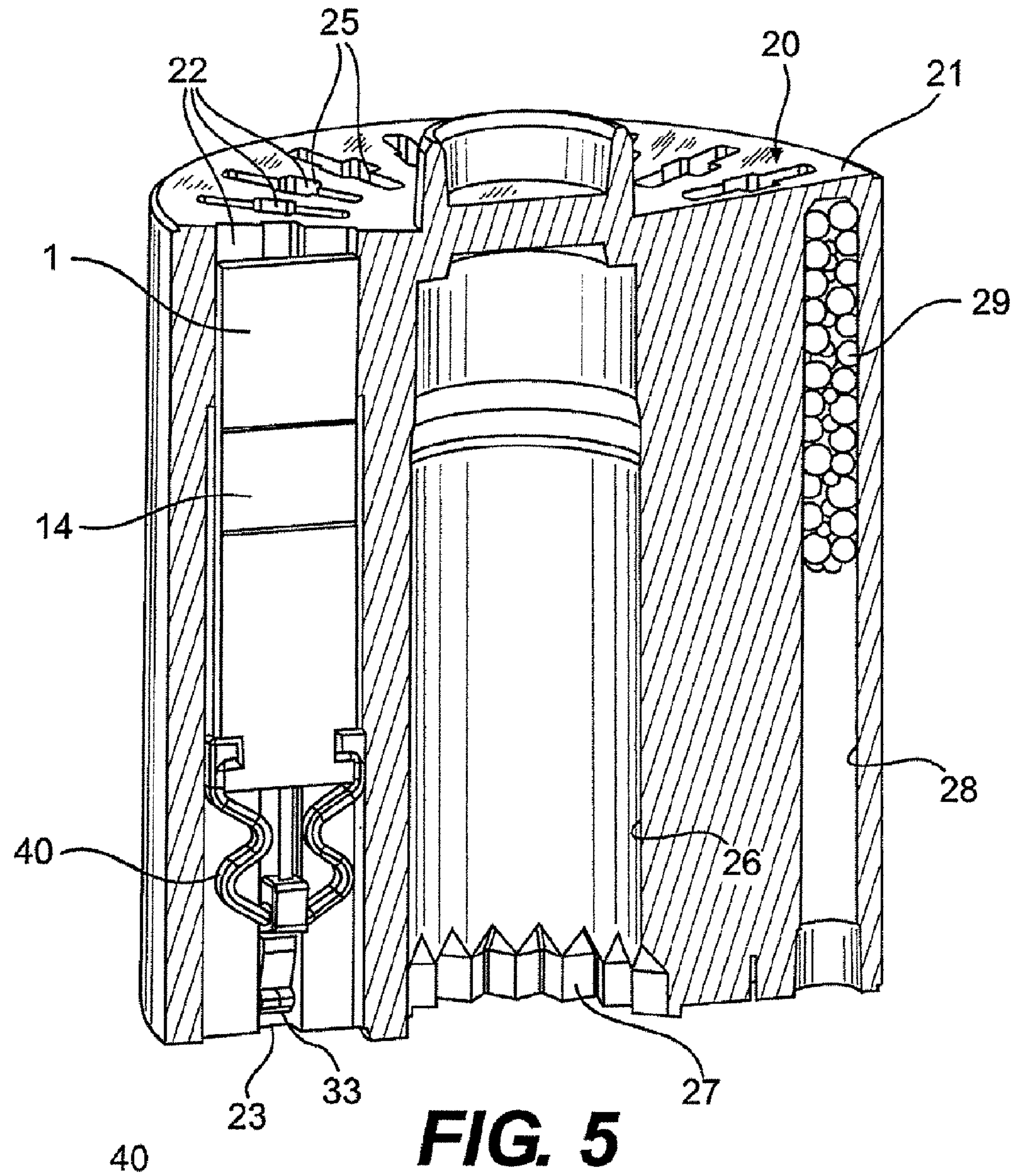
FIG. 5 is a perspective view in partial cross-section of a different embodiment of a storage container for holding test elements.
Figure 6:
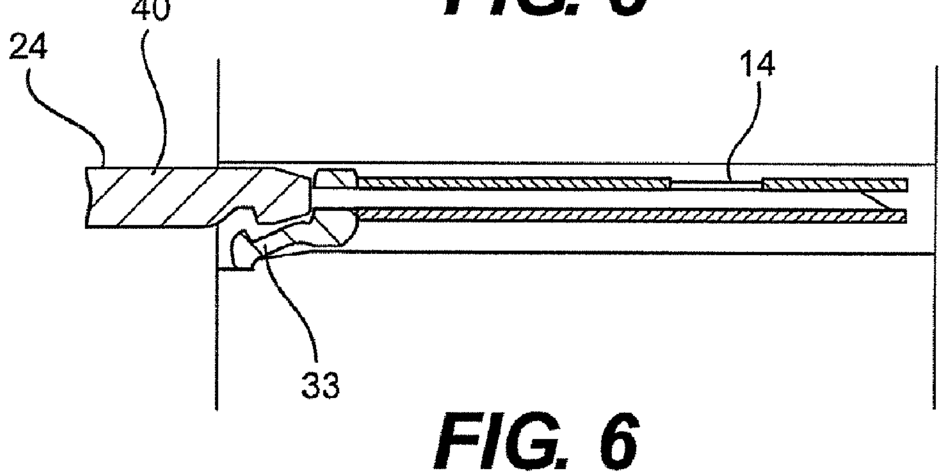
FIG. 6 is a cross-sectional view of a carriage of the container of FIG. 5 and a spring brace which drives the carriage.

In the exemplary embodiment shown in FIGS. 5 and 6, a test element 1 can be positively connected similar to the previously described carriage 30 by a single holding claw 33 as a driving carrier with a single drive plunger for both forward and backward movement. A spring brace 40 is provided as a drive plunger to move or drive the test element 1. Of course, any number of other methods for storing test elements are conceivable such as those that are well-known in the art. The system is not limited to any special embodiments of a magazine and/or of a test element transport.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An analytical test element for determining presence or concentration of an analyte in a body fluid, comprising:

an application site adapted to receive a body fluid sample;

a detection area spaced from the application site and configured for analyzing the body fluid sample;

a transport element disposed between the application site and the detection area, the transport element being configured to transport the body fluid sample from the application site to the detection area; and a contamination area at least partially adjoining and surrounding the application site, the contamination area comprising an adhesive exposed for contact by the body fluid sample and adapted to adhere a dried portion of the body fluid sample to the analytical test element.

2. The analytical test element of claim 1, wherein the adhesive comprises polyvinyl acetate.

3. The analytical test element of claim 1, wherein the adhesive contains dextrin or caoutchouc.

4. The analytical test element of claim 1, wherein the adhesive includes water soluble components.

5. The analytical test element of claim 1, wherein the transport element comprises a capillary channel.

6. The analytical test element of claim 1, wherein the transport element includes a hydrophilic coating.

7. The analytical test element of claim 1, further comprising a cover layer and a carrier layer which define top and bottom exposed surfaces of the analytical test element, respectively, the exposed surfaces being at least partially covered with the adhesive.

8. The analytical test element of claim 7, further comprising a spacer layer disposed between the carrier layer and the cover layer, the spacer layer defining a recess which cooperates with the cover and carrier layers to form the transport element.

9. The analytical test element of claim 1, wherein the adhesive substance is applied to the application site.

10. The analytical test element of claim 1, wherein the application site is essentially free of the adhesive.

11. A method of using an analytical test element to determine the presence or concentration of an analyte in a body fluid sample, the method comprising:

applying a body fluid sample to an application site of the analytical test element;

transporting some of the body fluid sample from the application site to a detection area of the analytical test element;

analyzing the body fluid sample transported to the detection area for the presence or concentration of the analyte; and adhering a dried portion of the body fluid sample to an adhesive disposed in a contamination area, the contamination area at least partially adjoining and surrounding the application area.

12. The method of claim 11, further comprising dissolving some of the adhesive into the sample before the transporting step.

13. The method of claim 11, further comprising completing the analyzing step before body fluid dries on the contamination area.

14. The method of claim 11, further comprising using capillary action to transport the body fluid to the detection area.

15. The method of claim 14, wherein the adhesive includes polyvinyl acetate.

16. The method of claim 11, wherein the adhesive includes one or more of dextrin, caoutchouc and water soluble components.

* * * * *